(12) United States Patent
Müller

(10) Patent No.: US 6,777,556 B2
(45) Date of Patent: Aug. 17, 2004

(54) PROCESS FOR PREPARING 2-HALOALKYLNICOTINIC ACIDS

(75) Inventor: Peter Müller, Odenthal (DE)

(73) Assignee: Bayer Chemicals AG, Leverkusen (DE)

( * ) Notice: Subject to any disclaimer, the term of this patent is extended or adjusted under 35 U.S.C. 154(b) by 0 days.

(21) Appl. No.: 10/373,537

(22) Filed: Feb. 24, 2003

(65) Prior Publication Data

US 2003/0176468 A1 Sep. 18, 2003

(30) Foreign Application Priority Data

Feb. 28, 2002 (DE) .......................................... 102 08 955

(51) Int. Cl.⁷ .......................................... C07D 213/14
(52) U.S. Cl. ..................................................... 546/250
(58) Field of Search ........................................ 546/250

(56) References Cited

U.S. PATENT DOCUMENTS

| 6,214,878 B1 | 4/2001 | Bernardon et al. ......... 514/569 |
| 2002/0019527 A1 | 2/2002 | Wang et al. ................. 544/360 |
| 2003/0083502 A1 * | 5/2003 | Pozenok ..................... 546/250 |

FOREIGN PATENT DOCUMENTS

| EP | 385 351 | 2/1990 |
| EP | 902 026 | 9/1998 |
| UA | 2 065 121 | 6/1981 |
| WO | 00/39094 | 7/2000 |

OTHER PUBLICATIONS

Crom and Hammond, "Organic Chemistry", McGraw Hill Book Co., NY (1964) 2nd ed. pp. 565–567.*
Tetrahedron Lett. 39, (month unavailable) 1998, pp. 7965–7966, Jason WB Cooke, Mark J. Colemann Darren M. Caine and Kevin P. Jenkins, "Efficient synthesis of 2–trihalomethyl–5–cyanopyridines".
J. Heterocycl. Chem. , 32, Mar.–Apr. 1995, pp. 543–545, Maria Teresa Cocco, Cenzo Congiu, and Valentina Onnis, "Synthesis of Triflouromethylated Pyridinecarbonitriles".
Heterocycles, vol. 46, Marcj 1997 pp. 129–132, Etsuji Okada, Tatsuhiko Kinomura, Yukio Higashiyama, Hiroshi Takeuchi and Masaru Hojo, "A Simple and Convenient Synthetic Method forα–Triflouromethypyridines".

* cited by examiner

Primary Examiner—Patricia L. Morris
(74) Attorney, Agent, or Firm—Godfried R. Akorli; Diderico van Eyl

(57) ABSTRACT

The present invention relates to a process for preparing 2-haloalkylnicotinic acids and haloalkylnicotinic acid derivatives starting from halomethyl-substituted enones and 3-dialkylaminoacrylic esters and also to intermediates of the process according to the invention.

14 Claims, No Drawings

PROCESS FOR PREPARING 2-HALOALKYLNICOTINIC ACIDS

BACKGROUND OF THE INVENTION

1. Field of the Invention

The present invention relates to a process for preparing 2-haloalkylnicotinic acids and derivatives thereof and also to intermediates.

2. Brief Description of the Prior Art

2-Haloalkylnicotinic acids and their derivatives, particularly 2-trifluoromethylnicotinic acid, are valuable intermediates, for example for preparing active pharmaceutical ingredients and agrochemicals.

Tetrahedron Lett. 1998, 39, 7965 and J. Heterocycl. Chem. 1995, 32, 543 disclose that 2-halomethyl-5-cyanopyridines can be prepared from halomethyl-substituted enones and enaminonitriles. These may be converted in a manner known per se, for example by hydrolysis, to the corresponding nicotinic acids. A disadvantage of industrial application of this process is that the preparation of the corresponding enaminonitriles is costly and inconvenient. Hence the resulting products are expensive.

According to Heterocycles 1997, 46, 129, 2-trifluoromethylnicotinic acids may be prepared from β-trifluoroacetylvinylamine and substituted 1,3-diketones. However, it is generally only possible by this process to obtain nicotinic acids substituted in the 6-position., From this, it is possible to obtain compounds unsubstituted in the 6-position, for example by reductive dehalogenation of the 6-halo compounds. Owing to the high number of reaction steps, this process is also uneconomic.

Alternatively, according to WO 00/39094, substituted β-acetylvinylamines and β-ketoesters can be converted to the corresponding nicotinic esters. Owing to the costly and inconvenient preparation of the isolated β-acetylvinylamines, this process is also unsuitable for industrial application.

There was therefore a need to develop a process which, starting from readily available reactants, makes it possible to prepare the 2-haloalkylnicotinic acids in few steps.

SUMMARY OF THE INVENTION

A process has now been found for preparing 2-haloalkylnicotinic acids and 2-haloalkyl acid derivatives, which is characterized in that a) compounds of the general formula (I)

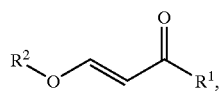

(I)

in which
$R^1$ is $C_1$–$C_{12}$-haloalkyl and
$R^2$ is $C_1$–$C_{12}$-alkyl are reacted with compounds of the general formula (II)

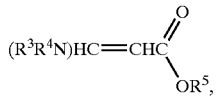

(II)

in which
$R^3$, $R^4$ and $R^5$ are each independently $C_1$–$C_{12}$-alkyl to give compounds of the general formula (III)

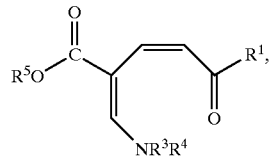

(III)

in which
$R^3$, $R^4$, $R^5$ and $R^5$ are each as defined above, and b) the compounds of the general formula (III) are reacted with ammonia or ammonium salts to give compounds of the general formula (IV)

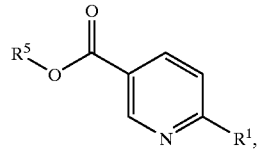

(IV)

in which
$R^1$ and $R^5$ are as defined above, and c) optionally, the compounds of the general formula (IV) are hydrolysed to give compounds of the general formula (V)

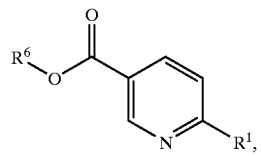

(V)

in which
$R^1$ is $C_1$–$C_{12}$-haloalkyl and
$R^6$ is M or hydrogen, where M is one equivalent of an alkali metal or half an equivalent of alkaline earth metal.

The scope of the invention also encompasses the compounds of the general formulae (III) and (IV) themselves.

DETAILED DESCRIPTION OF THE INVENTION

The invention is described more fully hereunder with particular reference to its preferred embodiments. For the purposes of the invention, alkyl is a straight-chain or cyclic, branched or unbranched alkyl radical. For example and with preference, $C_1$–$C_{12}$-alkyl is methyl, ethyl, n-propyl, isopropyl, n-butyl, tert-butyl, n-pentyl, cyclohexyl, n-hexyl, n-octyl, isooctyl, n-decyl and n-dodecyl.

For the purposes of the invention, haloalkyl means a straight-chain or cyclic, branched or unbranched alkyl radical which is substituted once or more than once overall in the α-position at least singly by halogen atoms which may each be selected independently from the group of fluorine, chlorine and bromine.

For example and with preference, $C_1$–$C_{12}$-haloalkyl is fluoromethyl, difluoromethyl, trifluoromethyl, tribromomethyl, dibromofluoromethyl, bromodifluoromethyl, trichloromethyl, dichlorofluoromethyl, chlorodifluoromethyl, trifluoromethyl, tribromomethyl, dibromofluoromethyl, pentafluoroethyl and n-nonafluorobutyl.

It is pointed out that any desired combinations of preferred compounds are encompassed by the scope of the invention.

In the compounds of the general formula (I), $R^1$ is more preferably $C_1$–$C_4$-haloalkyl, even more preferably trifluoromethyl, trichloromethyl, dichlorofluoromethyl and pentafluoroethyl, trifluoromethyl being still further preferred.

In the compounds of the general formula (I), $R^2$ is more preferably $C_1$–$C_4$-alkyl, even more preferably ethyl or methyl, ethyl being still further preferred.

Special mentioned is made of the following compounds of the general formula (I): 1,1,1-trifluoro-2-oxo-4-ethoxybut-3-ene, 1-bromo-1,1-difluoro-2-oxo-4-ethoxybut-3-ene, 1-chloro-1,1-difluoro-2-oxo-4-ethoxybut-3-ene and 1,1,1-trichloro-2-oxo-4-ethoxybut-3-ene.

In the compounds of the general formula (II), $R^3$ and $R^4$ are more preferably identical and are each $C_1$–$C_4$-alkyl, even more preferably identical and are each methyl or ethyl, methyl being still further preferred.

In the compounds of the general formula (II), $R^5$ is more preferably $C_1$–$C_4$-alkyl, even more preferably ethyl or methyl.

The following are illustrative examples of the compounds of the general formula (II): methyl 3-N,N-dimethylaminoacrylate, ethyl 3-N,N-diethylaminoacrylate, ethyl 3-N,N-dimethylaminoacrylate and methyl 3-N,N-diethylaminoacrylate.

The compounds of the general formula (I) are commercially available or can be synthesized by methods known from the literature or analogous thereto.

The compounds of the general formula (II) are likewise commercially available and can be synthesized by methods known from the literature (see, for example, WO 00/000460 or DE-OS (German published specification) 44 18 155) or analogous thereto.

Preference is given to carrying out the reaction of step a) in the presence of solvent. Examples of useful solvents include dipolar, aprotic solvents and mixtures which comprise dipolar, aprotic solvents. Examples of useful dipolar, aprotic solvents include nitriles such as acetonitrile, propionitrile, n- and i-butyronitrile, benzyl nitrile and benzonitrile, amides such as formamide, N-methylformamide, N,N-dimethylformamide, N,N-dimethylacetamide and N-methylpyrrolidone, esters such as methyl acetate, ethyl acetate or butyl acetate, sulphoxides such as dimethyl sulphoxide and sulphones such as sulpholane or mixtures thereof. The dipolar, aprotic solvents may also be used in mixtures, for example, with aliphatic and/or aromatic hydrocarbons and/or ethers. Particularly preferred dipolar, aprotic solvents are N,N-dimethylformamide and N,N-dimethylacetamide. Very particular preference is given to N,N-dimethylformamide. The amount of solvent used is not critical, and preference is given to using from 250 to 500 ml per mole of the particular compound of the general formula (I).

To carry out step a), for example, the particular compound of the general formula (I) and the particular compound of the general formula (II) may be used in a molar ratio of, for example, 0.3:1 to 5:1, preferably 0.5:1 to 2:1, more preferably 0.9 to 1.1 and most preferably in equimolar amounts.

The reaction temperature in step a) may be, for example, 0 to 100° C., preferably 20 to 80° C. and more preferably 30 to 50° C.

The reaction time for step a) may be, for example, 5 min to 48 h, and preference is given to 4 to 12 h.

Step a) of the process according to the invention may be carried out, for example, at a pressure of 0.5 to 100 bar, and preference is given to ambient pressure.

In this way, compounds of the general formula (III) are obtained

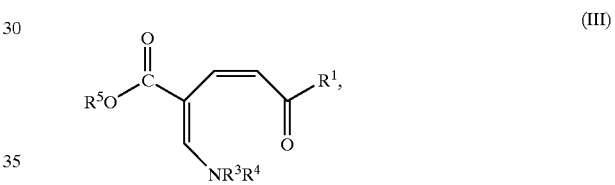

(III)

in which the $R^1$, $R^3$, $R^4$ and $R^5$ radicals have the same meanings and preferred ranges as specified under the general formulae (I) and (II). The following are illustrative examples of the compounds: ethyl 2-dimethylaminomethylene-6,6,6-trifluoro-5-oxo-3-hexenoate, ethyl 2-dimethylaminomethylene-6-bromo-6,6-difluoro-5-oxo-3-hexenoate, ethyl 2-dimethylaminomethylene-6-chloro-6,6-difluoro-5-oxo-3-hexenoate, ethyl 2-dimethylaminomethylene-6,6,6-trichloro-5-oxo-3-hexenoate.

The compounds of the general formula (III) may either be isolated or preferably directly reacted further.

Step b) comprising the reaction with ammonia or ammonium salts, preferably ammonium salts is carried out. In a preferred embodiment of the process according to the invention, the reaction solution from step a) is used directly in step b). Alternatively, isolated compounds of the general formula (E) may also be used.

Based on the compound of the general formula (II) originally used, for example, 0.3 to 10 mol, preferably 0.9 to 2.5 mol and more preferably 1.0 to 1.5 mol, of ammonia or ammonium salt may be used.

Particular preference is given to using ammonium salts of the general formula (VI)

(VI), in which

X is a monoanion of an inorganic or organic acid, or mixtures of such ammonium salts.

X is preferably a halide or a monoanion of a carboxylic acid.

X is more preferably chloride, bromide or acetate, most preferably acetate.

The reaction temperature in step b) may be, for example, 0 to 100° C., preferably 20 to 80° C. and more preferably 30 to 50° C.

The reaction time for step b) may be, for example, 5 min to 48 h, and preference is given to 30 min to 4 h.

Step b) of the process according to the invention may, for example, be carried out at pressure of 0.5 to 100 bar, and preference is given to atmospheric pressure.

Workup methods known per se provide compounds of the general formula (IV) in the manner according to the invention which may optionally be subjected to step c), the hydrolysis.

In the general formula (IV), $R^1$ and $R^5$ each have the same meanings and preferred ranges as were specified under the general formulae (I) and (II). Illustrative examples of the compounds are: ethyl 2-trifluoromethylnicotinate, ethyl 2-bromodifluoromethylnicotinate, ethyl 2-chlorodifluoromethylnicotinate, ethyl 2-trichloromethylnicotinate.

In a preferred embodiment of the process according to the invention, the workup may be carried out in such a manner that the reaction solution obtained in step b) is admixed with water and the organic phase, or the organic phases after repeated extraction with a water-immiscible or only sparingly water-miscible solvent, are concentrated by evaporating the solvent.

Examples of water-immiscible or only sparingly water-miscible solvents include aromatic solvents, for example benzene, toluene, o-, m-, p-xylene, chlorinated hydrocarbons, for example dichloromethane, chloroform, carbon tetrachloride, ethers, for example diethyl ether and tert-butyl methyl ether, esters such as methyl acetate, ethyl acetate or butyl acetate.

The crude products obtained in this way may be further purified, for example, by distillation at room temperature, and solid products also by crystallization or sublimation. However, it is also possible to directly hydrolyse the crude products.

Preference is given to carrying out the hydrolysis of the compound of the general formula (IV) in the presence of bases.

Preference is further given to using solvents in the hydrolysis.

Examples of useful solvents for step c) include: water, organic solvents and mixtures thereof. Examples of organic solvents include: aliphatic, alicyclic and aromatic hydrocarbons such as petroleum ether, hexane, heptane, cyclohexane, methylcyclohexane, benzene, toluene, xylene and decalin, ethers such as diethyl ether, diisopropyl ether, methyl t-butyl ether and methyl t-amyl ether, dioxane, tetrahydrofuran, 1,2-dimethoxyethane, 1,2-diethoxyethane, diethylene glycol dimethyl ether and anisole, and alcohols such as methanol, ethanol, n- and i-propanol, n-, iso-, sec- and tert-butanol, ethanediol, propane-1,2-diol, ethoxyethanol, methoxyethanol, diethylene glycol monomethyl ether and diethylene glycol monoethyl ether. Preferred solvents are alcohols.

Particular preference is given to ethanol or methanol.

To hydrolyse, for example 40 to 1000 ml, preferably 90 to 200 ml, of solvent may be used per mole of the compounds of the general formula (IV). Larger amounts of solvents are possible, but uneconomic.

For example and with preference, the bases used are alkali metal hydroxides, for example lithium hydroxide, sodium hydroxide, potassium hydroxide, for example in the form of aqueous solutions, or alkaline earth metal hydroxides, for example calcium hydroxide, or any desired mixtures thereof.

Particular preference is given to sodium hydroxide.

To hydrolyse, for example 0.5 to 10 mol of base, preferably 1.5 to 2.5 mol of base, may be used per mole of the compounds of the general formula (IV).

The reaction temperature for step c) may be, for example, 0 to 200° C., preferably 20 to 120° C., more preferably 50 to 100° C.

Step c) of the process according to the invention may, for example, be carried out at a pressure of 0.5 to 100 bar, and preference is given to ambient pressure.

In the manner according to the invention, step c) provides compounds of the general formula (V), in which $R^2$ is M or hydrogen.

When the hydrolysis is carried out in the presence of a base, as is preferred in accordance with the invention, compounds of the general formula (V) are obtained in which M is the cation of the base used.

These may either be isolated or converted to compounds of the general formula (I) in which $R^2$ is hydrogen by acidifying.

The acidification may be carried out, for example, with the aid of acidic salts and/or acids.

For example and with preference, useful acids are inorganic acids, for example hydrochloric acid.

The further workup and isolation of the reaction products may be effected by methods known per se.

Compounds of the general formula (V) in which $R^2$ is hydrogen may preferably be further purified by crystallization, distillation or by removing the volatile components, optionally under reduced pressure.

The compounds of the general formulae (IV) and (V) are especially useful for preparing pharmaceuticals and agrochemicals.

The process according to the invention facilitates the advantageous preparation of 2-haloalkylnicotinic acid and 2-haloalkylnicotinic acid derivatives in a highly efficient process in very few steps and without any special precautions. The invention is further described the following illustrative but non-limiting examples.

EXAMPLES

Example 1

Preparation of 1,1,1-trifluoromethyl-2-oxo-4-ethoxy-but-3-ene

A mixture of 1133 g of ethyl vinyl ether and 1130 g of pyridine was added dropwise to 3000 g of trifluoroacetic anhydride in 4200 ml of tert-butyl methyl ether at −10° C. to 0° C. The mixture was then stirred at room temperature overnight until complete conversion (GC). The reaction mixture was filtered and the filtrate admixed with a spatulatip of the radical scavenger Junol and concentrated at 40° C. and a pressure of 100 mbar. This reaction was repeated twice. All three batches were combined (9024.5 g of crude material) and distilled under atmospheric pressure using a 1 m randomly packed column. 5960 g of product were obtained. According to GC, the product was 97.9% pure. This corresponds to a yield of 81% of theory.

Example 2

Preparation of Ethyl 2-trifluoromethylnicotinate 3583.6 g of ethyl 3,3-dimethylaminoacrylate were gradually added dropwise at 40° C. to a solution of 4500 g of the product obtained in Example 1 in 9000 ml of N,N-dimethylformamide and stirred to complete conversion (12 h).

The solution of ethyl 2-dimethylaminomethylene-6,6,6-trifluoro-5-oxo-3-hexenoate obtained in this way was admixed with 2893.8 g of ammonium acetate and again stirred to complete conversion (1.5 h). The reaction mixture was diluted with 8 l of water, the organic phase was removed and the aqueous phase extracted twice with 500 ml of toluene each time. The combined organic phases were concentrated. 8294.5 g of crude product were obtained. The crude material was then distilled under reduced pressure. 3402 g of product having a boiling point of 64 to 67° C. at 0.07 to 0.09 mbar were obtained. According to GC, the product was 94.4% pure. The yield was accordingly 94% of theory.

Example 3

Preparation of 2-trifluoromethylnicotinic Acid

A mixture of 4782.5 g of 25% sodium hydroxide solution, 1650 ml of ethanol and 3470 g of the product obtained according to Example 2 were stirred under reflux (80° C.) for 7 h. The reaction mixture was then added to ice and extracted twice with dichloromethane. The organic phase was removed and discarded. The aqueous phase was adjusted to a pH of about 4 using concentrated hydrochloric acid. The precipitated product was then filtered off with suction. Afterwards, the filtrate was adjusted to a pH of about 2 using concentrated hydrochloric acid and filtered off with suction. The combined solid charges were twice slurried with n-hexane, filtered off with suction and dried. 2717.4 g of product were obtained. According to GC, the product was over 99% pure. The yield was accordingly 95% of theory.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for preparing 2-haloalkylnicotinic acids and 2-haloalkylnicotinic acid derivatives, comprising reacting a) a compound of the formula (I)

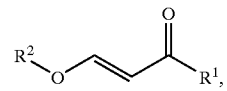

in which
$R^1$ is $C_1$–$C_{12}$-haloalkyl and
$R^2$ is $C_1$–$C_{12}$-alkyl
with a compound of the formula (II)

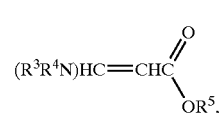

in which
$R^3$, $R^4$ and $R^5$ are each independently $C_1$–$C_{12}$-alkyl
to give a compound of the formula (III)

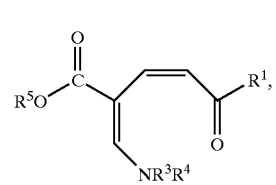

in which $R^1$, $R^3$, $R^4$ and $R^5$ are each as defined above, and
b) reacting a compound of the formula (III) with ammonia or ammonium salts to give compounds of formula (IV)

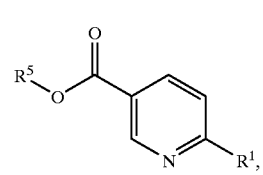

in which
$R^1$ and $R^5$ are as defined above,
c) optionally hydrolysing the compounds of formula (IV) to give compounds of formula (V)

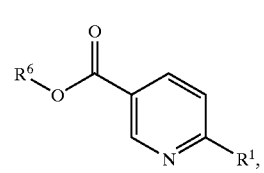

in which
$R^1$ is $C_1$–$C_{12}$-haloalkyl and
$R^6$ is M or hydrogen, where M is one equivalent of an alkali metal or half an equivalent of alkaline earth metal.

2. Process according to claim 1, characterized in that the compounds of the formula (I) used are those in which $R^1$ is fluoromethyl, difluoromethyl, trifluoromethyl, tribromomethyl, dibromofluoromethyl, bromodifluoromethyl, trichloromethyl, dichlorofluoromethyl, chlorodifluoromethyl, trifluoromethyl, tribromomethyl, dibromofluoromethyl, pentafluoroethyl or n-nonafluorobutyl.

3. Process according to claim 1, characterized in that the compounds of the formula (I) used are those in which $R^2$ is ethyl or methyl.

4. Process according to claim 1, characterized in that the compounds of the formula (II) used are those in which $R^3$ and $R^4$ are identical and are each $C_1$–$C_4$-alkyl.

5. Process according to claim 1, characterized in that the compounds of the formula (II) used are those in which $R^5$ is $C_1$–$C_4$-alkyl.

6. Process according to claim 1, characterized in that step a) is carried out in the presence of solvent.

7. Process according to claim 1, characterized in that the compounds of the general formula (I) and the compounds of the general formula (II) are reacted in step a) in a molar ratio of 0.3:1 to 5:1.

8. Process according to claim 1, characterized in that the reaction temperature in step a) is 0 to 100° C.

9. Process according to claim 1, characterized in that 0.3 to 10 mol of ammonium salt are used in step b), based on the compound of the formula (I) used in step a).

10. Process according to claim 1, characterized in that the ammonium salts used in step b) are those of the formula (VI)

$$NH_4X \qquad (VI)$$

in which X is a monoanion of an inorganic or organic acid, or mixtures of such ammonium salts.

11. Process according to claim 1, characterized in that the reaction temperature in step b) is 0 to 100° C.

12. Process according to claim 1, characterized in that step c) is the hydrolysis of a compound of the general formula (IV) to give compounds of the formula (V)

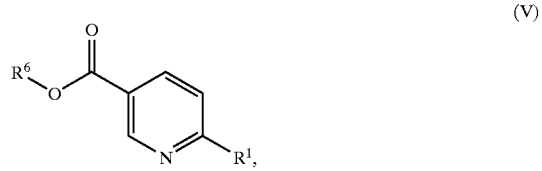

(V)

in which $R^6$ is hydrogen or M and M is an equivalent of an alkali metal or half an equivalent of alkaline earth metal.

13. Process according to claim 12, characterized in that step c) is carried out in the presence of base.

14. Process according to claim 13, characterized in that, to prepare compounds of the formula (V)

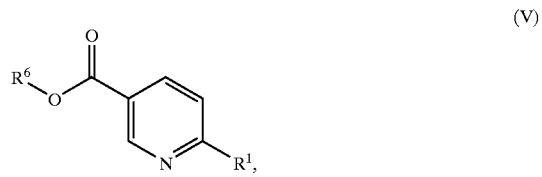

(V)

in which

M is hydrogen, and acidification is effected after step c).

* * * * *